(12) United States Patent
Grant

(10) Patent No.: US 10,874,435 B2
(45) Date of Patent: Dec. 29, 2020

(54) BONE SECUREMENT APPARATUS AND METHOD

(71) Applicant: William P. Grant, Virginia Beach, VA (US)

(72) Inventor: William P. Grant, Virginia Beach, VA (US)

(*) Notice: Subject to any disclaimer, the term of this patent is extended or adjusted under 35 U.S.C. 154(b) by 200 days.

(21) Appl. No.: 16/220,669

(22) Filed: Dec. 14, 2018

(65) Prior Publication Data

US 2019/0110818 A1 Apr. 18, 2019

Related U.S. Application Data

(62) Division of application No. 14/807,080, filed on Jul. 23, 2015, now Pat. No. 10,182,845.

(51) Int. Cl.
| | |
|---|---|
| *A61B 17/88* | (2006.01) |
| *A61B 17/68* | (2006.01) |
| *A61B 17/80* | (2006.01) |
| *A61B 17/86* | (2006.01) |

(52) U.S. Cl.
CPC ........ *A61B 17/683* (2013.01); *A61B 17/8057* (2013.01); *A61B 17/8061* (2013.01); *A61B 17/86* (2013.01); *A61B 2017/8655* (2013.01)

(58) Field of Classification Search
CPC combination set(s) only.
See application file for complete search history.

(56) References Cited

U.S. PATENT DOCUMENTS

| | | | |
|---|---|---|---|
| 2,496,126 A | 1/1950 | Haboush | |
| 5,938,664 A | 8/1999 | Winquist et al. | |
| 6,916,323 B2 | 7/2005 | Kitchens | |
| 7,135,023 B2 | 11/2006 | Watkins et al. | |
| 7,846,189 B2 | 12/2010 | Winquist et al. | |
| 7,951,176 B2 | 5/2011 | Grady, Jr. et al. | |
| 8,157,803 B1 | 4/2012 | Zirkle, Jr. et al. | |
| 8,267,976 B2 | 9/2012 | Biedermann et al. | |
| 8,317,846 B2 | 11/2012 | Bottlang | |
| 8,425,574 B2 | 4/2013 | Huebner et al. | |
| 8,425,575 B2 | 4/2013 | Huebner et al. | |
| 8,690,932 B2 | 4/2014 | Morris et al. | |
| 8,734,448 B2 | 5/2014 | Thakkar | |
| 8,734,494 B2 | 5/2014 | Simon et al. | |
| 8,911,482 B2 | 12/2014 | Lee et al. | |
| 2001/0000186 A1 | 4/2001 | Bramlet et al. | |
| 2009/0177240 A1 | 7/2009 | Perez | |
| 2014/0172025 A1* | 6/2014 | Vaughan ............ | A61B 17/1757 606/309 |

* cited by examiner

*Primary Examiner* — Sameh R Boles
(74) *Attorney, Agent, or Firm* — Law Office of Alan W. Cannon

(57) ABSTRACT

A bone securement apparatus includes a bone plate configured and dimensioned to be applied across a joint of at least two bones or a space between at least two bone fragments. The bone plate includes first and second openings. A beaming member is configured to pass through the first opening, and the beaming member includes a third opening. A support member is configured to pass through the second opening and the third opening.

14 Claims, 14 Drawing Sheets

BONE SECUREMENT APPARATUS AND METHOD

CROSS REFERENCE

This application is a division of pending U.S. application Ser. No. 14/807,080, filed Jul. 23, 2015, which is hereby incorporated herein, in its entirety, by reference thereto, and to which application we claim priority under 35 USC § 120.

FIELD OF THE INVENTION

The present invention relates to the field of fixture devices for bones for use in surgical procedures.

BACKGROUND OF THE INVENTION

Various orthopedic surgical procedures require the locking or securing together of adjacent bones or broken bones. In the field of foot and ankle surgery, indications for reconstruction including osteotomy or arthrodesis are well documented in the medical literature as the standard to alleviate pain and infection, minimize limb loss, and maximize physical capacity to return to all activities of daily living or sports.

Technically, the above-mentioned types of surgery are complicated by the reality of weight bearing of the extremity. The most salient issue involved with healing of foot osteotomies is the complex loadbearing which is seen in the foot uniquely. Specifically, body weight axes of force vector down whereas a supporting surface, i.e. the floor, pushes back up. A bending moment is created along the medial and lateral columns of the foot.

The medial column comprises the first metatarsal, medial cuneiform, navicular, and talus bones. The lateral column comprises the fifth metatarsal, fourth metatarsal, cuboid, and calcaneus bones. The joint surfaces of the aforementioned bones that articulate are, for the most part, flat. These bones are stabilized, therefore, by dense and extraordinarily strong ligaments in every possible anatomic arrangement; some linear, some oblique, some crisscross. Unless injured by trauma or metabolic diseases such as advanced diabetes, these ligaments provide excellent stability for a lifetime of gait. However, when they lose their function, the articular surfaces are destroyed rather quickly by the unremitting forces of tension on the plantar surfaces and compression on the dorsal surfaces of the ligaments and their attendant bones.

In the field of podiatry and orthopedics a variety of solutions to facilitate arthrodesis and fusion across the joint surfaces has been promoted over the years. Initial approaches used simple K wires, followed by internal wire fixation with the K wires. This provided a combination of cerclage and K wire; one for compression, the other for alignment. Subsequent to this we adopted the principles of rigid fixation with micromotion, minimization, and strict non-weight bearing for 6 weeks or longer were utilized to facilitate primary bone healing without callus. Unfortunately, this method has its limitations as well since most patients are unable to stay off their feet for 6 weeks. Diabetics with neuropathy are even more unaware of how they are standing on their foot. Noncompliance with the requirement to stay off the foot typically results in failure of the procedure.

Another approach was to revert to external fixation with an Ilizarov fixator to engender bound wire fixation in combination with internal fixation. This synergistic combination provided higher compression than either form on an isolated basis. In fact limited weight bearing can be encouraged during the perioperative period. External fixation has its limitations as well. Most surgeons do not want to use external fixation because of its technical difficulty, its foreboding appearance, and the requisite constant follow-up during the perioperative period in the doctor's office, which may be financially unreasonable for some practitioners.

Many of the currently trained surgeons in the U.S. practicing foot and ankle surgery refer the use of locking plate technology. This new technology has been alleged to simulate the rigidity engendered by an external fixator. Nevertheless locking plates have not been suggested to be tenable for immediate weight bearing even on a limited basis after for reconstruction. Some more advanced practitioners use a combination of screw fixation with a plate placed over it, but the possibility of motion at the arthrodesis site remains.

For example, one common procedure in foot surgeries is directed to securing together the adjacent first metatarsal and medial cuneiform bones. Using known procedures and surgical devices, a patient can be immobilized for extended periods. Common procedures used in these foot surgeries include the use of a plate fixation lapidus as illustrated in FIG. 3. As is evident in FIG. 3, a locking plate 510 is fixed into the top or dorsal side of the adjacent first metatarsal 2 and medial cuneiform 3 bones. That plate is screwed into the tops of those bones 2,3 with the locking screws 512 shown.

Alternatively, a crossing screw fixation for lapidus procedure may be used, as illustrated in FIG. 4. In this procedure, locking screws 522 are installed through the adjacent first metatarsal 2 and medical cuneiform 3 bones, respectively, and across the first metatarsal-cuneiform joint 4 in a crisscrossing pattern as shown in FIG. 4. The bones 2 and 3 as a result, are fixed together in an effort to protect against the compression and tension directions of force when the foot is stood upon. The compression 5 and tension 6 forces that are experienced by the foot when bearing load of the body are illustrated in FIG. 3.

Both the plate fixation lapidus and crossing screw fixation for lapidus procedures (shown in FIGS. 3 and 4, respectively) have limitations in view of the substantial stresses that are applied to those foot bones during normal ambulation by a patient. Accordingly, in each example, there is limited effectiveness for these repair types of surgery.

Grady, Jr. et al. in U.S. Pat. No. 7,951,176 discloses a bone plate for use in reducing a bone fracture of the femur. Bone anchors (screws) are passed through the bone plate and into the bone of the femur to secure the plate to the femur. The shafts of the bone screws may touch or nearly touch at the point of intersection, such that the first and second bone anchors form a truss. While this "truss" formation may provide additional support to the compression forces experienced in the femur, this construction does nothing to provide further support for tension forces such as those experienced in the foot under load bearing.

There is a continuing need for solutions for the ultimate stabilization of the arthrodesis site of the weight bearing column of the foot. The present invention provides such solutions as well as solutions for improving the stabilization provided by surgical procedures to secure broken bone portions or adjacent bones in other orthopedic fields.

SUMMARY OF THE INVENTION

According to one aspect of the present invention, a bone securement apparatus is provided that includes: a bone plate configured and dimensioned to be applied across a joint of at least two bones or a space between at least two bone fragments, the bone plate comprising first and second openings; a beaming member passing through said first opening, the beaming member comprising a third opening; and a support member passing through the second opening and the third opening.

In at least one embodiment, the bone plate, beaming member and support member form a triangular structure.

In at least one embodiment, the beaming member comprises a beaming screw, the beaming screw comprising threads at a distal end portion thereof, the threads configured to be screwed into bone.

In at least one embodiment, the support member comprises a support screw, the support screw comprising threads extending past the third opening, the threads configured to be screwed into bone.

In at least one embodiment, the beaming member comprises threads that mate with threads in the first opening.

In at least one embodiment, the support member comprises threads that mate with threads in the second opening.

In at least one embodiment, the third opening is threaded.

In at least one embodiment, the support member comprises threads that mate with the threaded third opening.

In at least one embodiment, the bone plate comprises at least one additional opening configured to receive a screw therethrough for fixing the bone plate to a bone.

In at least one embodiment, the bone plate further comprises fourth and fifth openings, the apparatus further comprising: a second beaming member passing through the fourth opening, the second beaming member comprising a sixth opening; and a second support member passing through the fifth opening and the sixth opening.

In at least one embodiment, the bone plate, beaming member and support member form a first triangular structure and the bone plate, second beaming member and second support member form a second triangular structure.

In at least one embodiment, the first and second triangular structures comprise locked segments independent of each other.

In at least one embodiment, the bone plate further comprises a fourth and the beaming member further comprises a fifth opening, the apparatus further comprising: a second support member passing through the fourth opening and the fifth opening.

In another aspect of the present invention, a method of implanting a bone securement apparatus includes: placing a bone plate across a joint of at least two bones or a space between at least two bone fragments, the bone plate comprising first and second openings; inserting a beaming member through the first opening, a portion of a first of the bones or bone fragments and a portion of a second of the bones or bone fragments; wherein the beaming member comprises a third opening that is positioned in the second of the bones or bone fragments upon the inserting; and inserting a support member through the second opening and the third opening.

In at least one embodiment, the method further includes attaching the beaming member to the second of the bones or bone fragments via threading on the beaming member.

In at least one embodiment, the method further includes attaching the support member to the second of the bones or bone fragments via threading on the support member.

In at least one embodiment, the method further includes threading the support member into mating threads in the third opening.

In at least one embodiment, the method further includes attaching the bone plate to at least one of the first and second bones or bone fragments by inserting a locking screw through at least one additional opening in the bone plate and threading the locking screw into the at least one of the first and second bones or bone fragments.

In at least one embodiment, the bone plate, beaming member and support member form a triangular structure.

In at least one embodiment, the bone plate further comprises fourth and fifth openings, the method further includes: inserting a second beaming member through the fourth opening, and into at least one of the bones or bone fragments or at least a third bone or bone fragment and at least a third bone fragment, wherein the second beaming member comprises a sixth opening; and inserting a second support member through the fifth opening and the sixth opening.

In at least one embodiment, the first bone or bone fragment comprises a first metatarsal bone and the second bone or bone fragment comprises a medial cuneiform bone.

In at least one embodiment, the first bone or bone fragment comprises a first metatarsal bone, the second bone or bone fragment comprises a medial cuneiform bone, the at least one of the bones or bone fragments comprises the medial cuneiform bone and the at least a third bone or bone fragment comprises at least one of a navicular bone and a talus bone.

These and other features of the invention will become apparent to those persons skilled in the art upon reading the details of the apparatus and methods as more fully described below.

DETAILED DESCRIPTION OF THE INVENTION

Figure 1A:
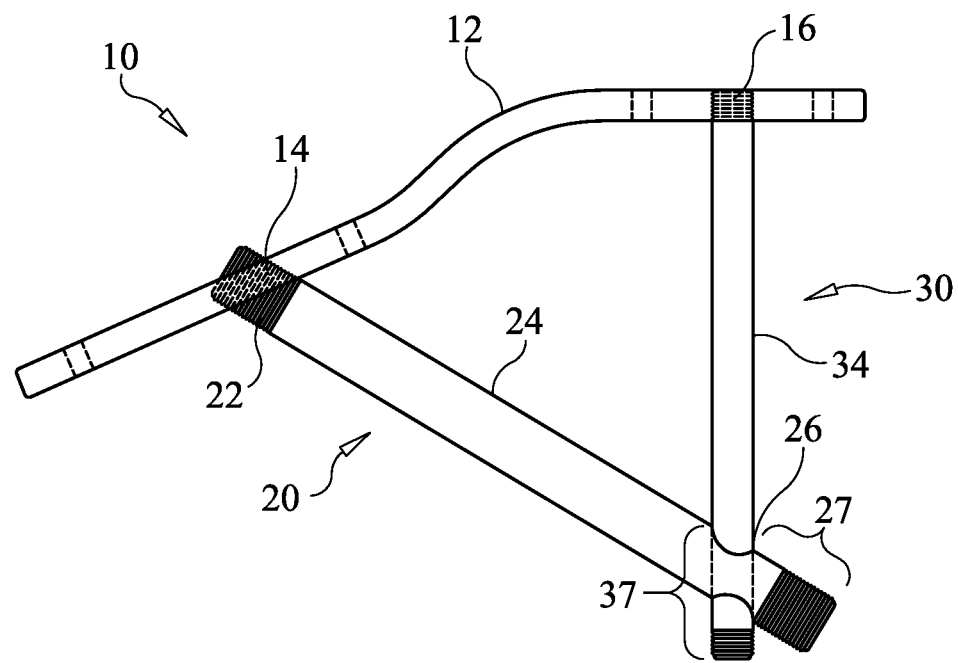
FIG. 1A illustrates a securement apparatus in an assembled state according to an embodiment of the present invention.

Before the present apparatus and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a screw" includes a plurality of such screws and reference to "the bone" includes reference to one or more bones and/or bone fragments and equivalents thereof known to those skilled in the art, and so forth.

The publications discussed herein are provided solely for their disclosure prior to the filing date of the present application. The dates of publication provided may be different from the actual publication dates which may need to be independently confirmed.

The present invention provides a triangular structure using interlocking components for securing two or more adjacent bones or broken bone fragments together. In at least one embodiment, a locking plate is fixed across an outer surface of two adjacent bones. The plate is itself fixed with locking screws to the respective adjacent bones. Additionally, two further screws are used in connection with the plate to create a triangular, rigid device. The two screws each pass through and are fixed to the plate and are also attached to each other to create the rigid, triangular structure. This rigid, triangular support will effectively rigidly secure the two adjacent bones and prevent any unwanted or undesirable compression or tension that is ordinarily present between the bones.

Referring now to FIG. 1A a securement apparatus 10 is shown in an assembled state according to an embodiment of the present invention. A locking plate 12 is configured to be placed against the bones or bone segments to be secured. Plate 12 can be bent or configured in a shaped designed to generally conform to the surfaces of the bones or bone fragments to be joined. In the embodiment shown in FIG. 1A, plate 12 has two bends along a medial portion thereof so as to shape the plate to conform to the proximal portion to the medial cuneiform bone 3 of the foot, and to generally conform the distal portion to the first metatarsal bone 2 of the foot. It is noted that the present invention is not limited to the shape of plate 12 shown in FIG. 1A, as different shapes may be employed for joining bones or fragments of bones other than the medial cuneiform and first metatarsal. In the embodiment of FIG. 1A, plate 12 has a length of about 30 mm but may be in the range of from about 15 mm to about 50 mm or from about 4 cm to about 10 cm and accommodate shapes for a variety of anatomical presentation. The thickness of plate 12 in FIG. 1A is about 1.25 mm, but may be in the range of from about 1.0 mm to about 2.0 mm or from about 0.1 cm to about 0.5 cm. The width of the plate 12 in FIG. 1A is about 12 mm, but may be in the range of from about 8 mm to about 25 mm or from about 1 cm to about 2.5 cm. Plate 12 in FIG. 1A is made of machined implant grade stainless steel, but could alternatively be made of machined Titanium 6Al-4V ELI, implant grade additive manufacturing materials such as Titanium Grade 2 or Osteo-Fab PEKK (polyetherketoneketone).

Figure 1B:
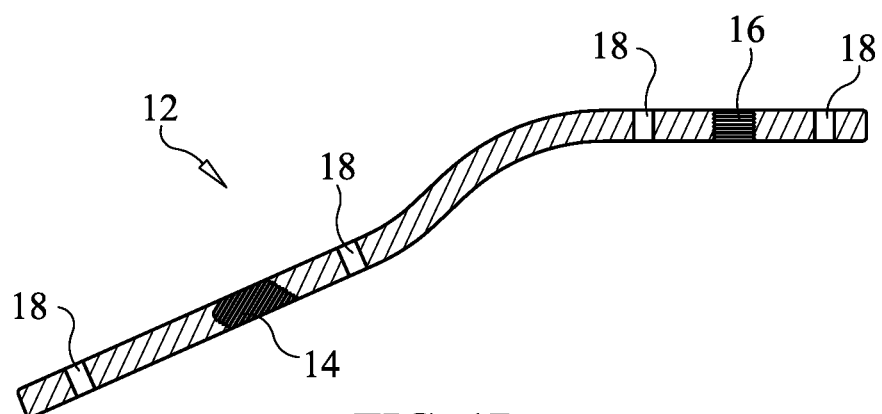
FIG. 1B is a longitudinal sectional view of the locking plate shown in FIG. 1A.
Figure 1C:
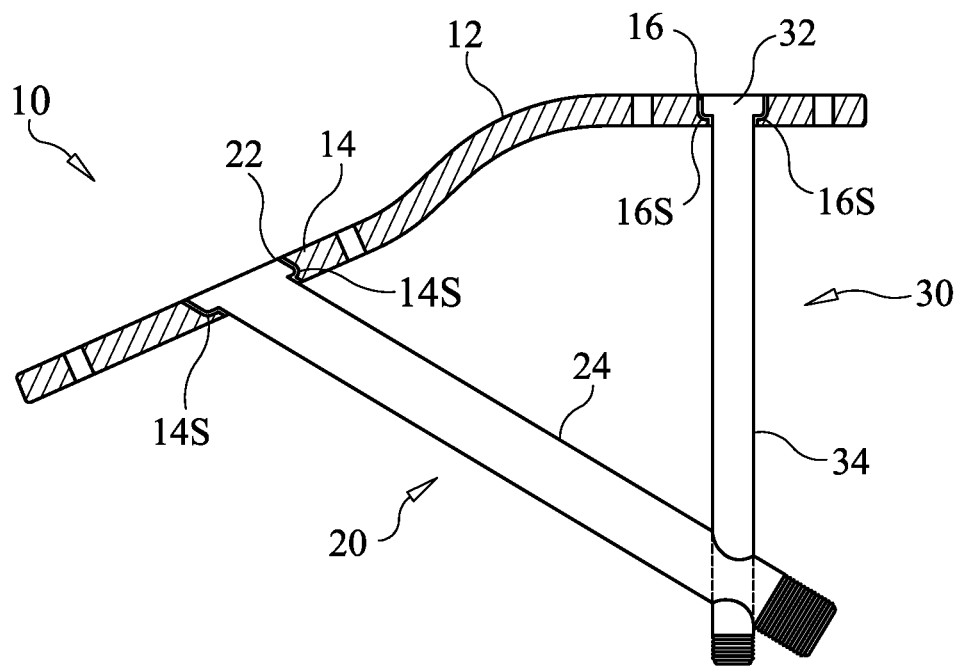
FIG. 1C shows a securement apparatus in which openings in the locking plate for receiving members 20 and 20 have smooth walls, according to an embodiment of the present invention.
Figure 1D:
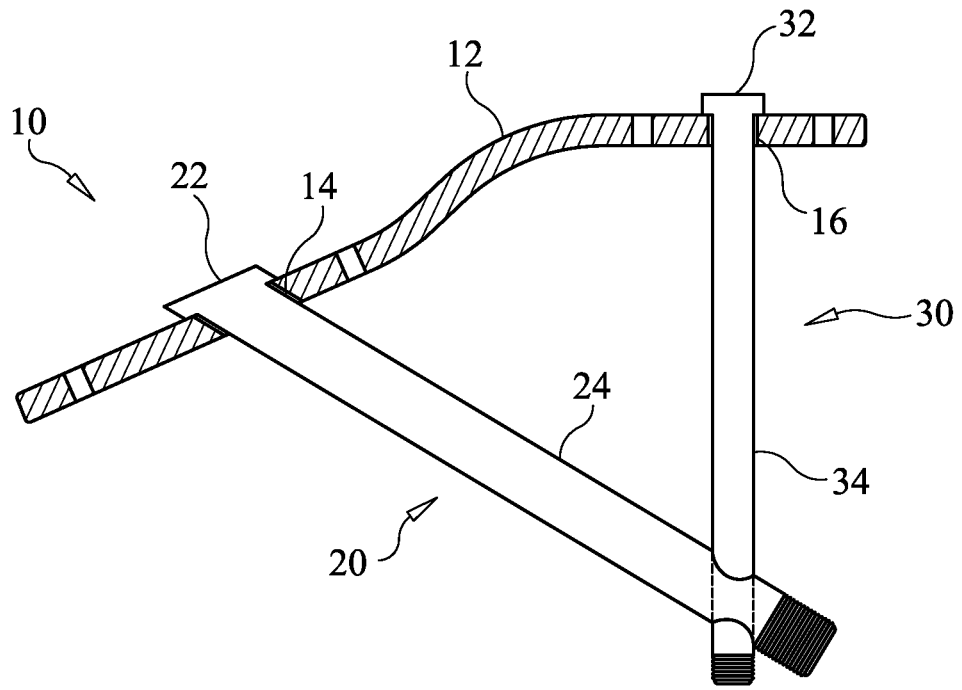
FIG. 1D Shows a securement apparatus in which openings in the locking plate are sized to allow shafts of members 20, 30 to pass through, but prevent heads therefor from entering the openings, according to an embodiment of the present invention.

Locking plate 12 includes first and second threaded openings 14, 16 see FIG. 1B) for allowing beaming screw 20 and support screw 30 to pass therethrough, respectively, and lock to the locking plate via mating threads or cam lock or morse taper lock depending on the material used. For example, a ¾ or single turn locking feature can be used for locking. Alternatively, the walls of openings 14,16 can be smooth (unthreaded) and configured to allow the shafts of the screws 20, 30 to pass therethrough, but not the heads of the screws 20, 30. FIG. 1C shows an embodiment in which openings 14, 16 have smooth walls and are configured to receive heads 22, 32 of screw 20, 30. Shoulders 14S, 16S formed at the bases of openings 14, 16 extend into the openings 14,16, effectively reducing the cross-sectional area of the opening so that the shafts 24, 34 are allowed to pass through, but the heads 22, 32 are prevented from passing the shoulders 14S, 16S. FIG. 1D shows another embodiment in which openings 14, 16 are sized to allow shafts 24, 34 to pass through, but prevent heads 22, 32 from entering the openings 14, 16, so that the heads 22, 32 are compressed against the top surface of the plate 12 in the assembled, locked configuration.

Locking plate 12 may optionally include through holes 18 as shown in FIG. 1B to allow locking screws to be screwed into the bone that the locking plate 12 contacts, thereby locking the locking plate 12 against the bone.

The apparatus 10 further includes a beaming screw 20 having a distal end portion and a proximal end portion with a shaft 20 extending therebetween. Beaming screw 20 in FIG. 1A is made of machined implant grade stainless steel, but could alternatively be made of machined Titanium 6Al-4V ELI, implant grade additive manufacturing materials such as Titanium Grade 2 or OsteoFab PEKK. In the embodiment of FIG. 1A, shaft 24 of beaming screw 20 has an outside diameter of about 5 mm and beaming screw 20 has a length of about 85 mm. In alternative embodiments, shaft 24 can have any diameter value within the range of from about 4.5 mm to about 6.5 mm and the length can be any value within the range from about 30 mm to about 100 mm, or within a range of from about 20 mm to about 50 mm. The cannula 27 in screw 20 allows it to be passed over a guide such as a K wire, as described in more detail below.

In the embodiment of FIG. 1A, beaming screw 20 includes an opening 26 having a diameter dimensioned to allow the shaft of support screw 30 to pass therethrough. In one embodiment, opening 26 has a diameter of about 3.5 mm, but may alternatively be in a range of from about 2.5 mm to about 5 mm. In one embodiment, the opening 26 is threaded and the support screw 30 is attached to the beaming screw 20 by mating engagement of the threads I the opening 26 with threads on the support screw 30. In another embodiment, the support screw 30 slides through the opening 30 and support screw 20 and beaming screw 30 are locked together as both are engaged with the plate 12 and the threaded distal end portions of the screws 20, 30 are anchored into bone. Optionally, the support screw 30 can have a relatively narrower tip 30T tapering 30P to a larger outside diameter 30D of the shaft so that the support screw tip easily enters and passes through the opening 26 and then forms a friction fit at the appropriate length along the shaft, see FIG. 1H. The distal end portion 27 is threaded to allow the beaming screw to be torqued into and anchored to bone. The proximal end portion includes head 22, which is threaded in the embodiment of FIG. 1A to mate with mating threads in the opening 16 to lock the head 22 to the plate 12.

Figure 1E:
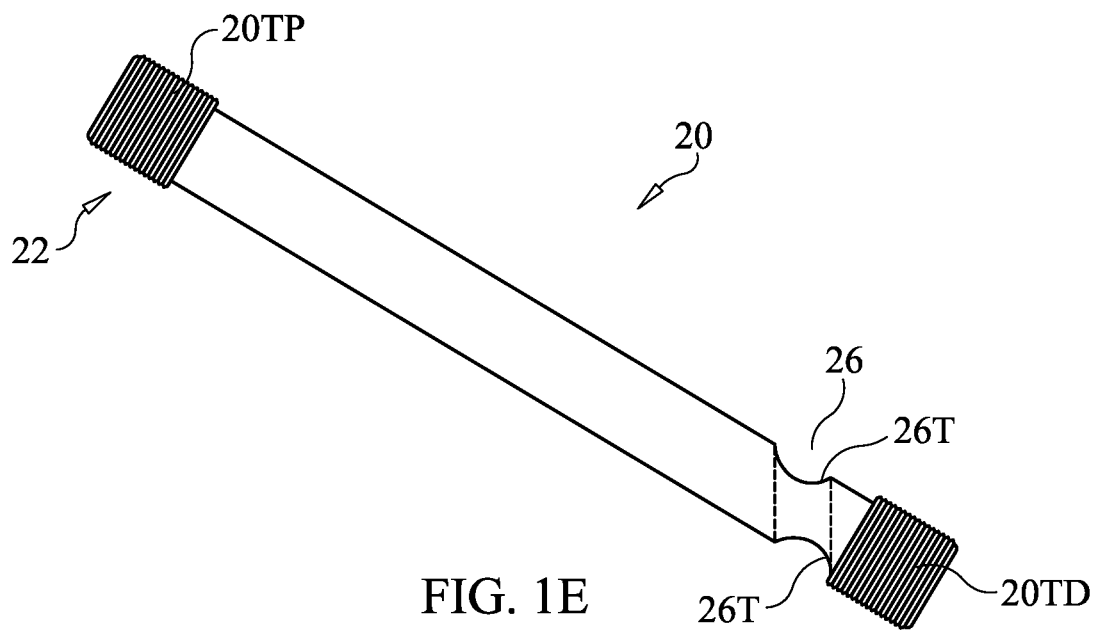
FIG. 1E illustrates a beaming screw according to an embodiment of the present invention.

FIG. 1E shows an embodiment of beaming screw 20 in which the distal end portion of screw 20 is threaded 20TD and the head 22 of the screw 20 at the proximal end portion is threaded 20TP. The opening 26 is also threaded 26T. In alternative embodiments, head 22 can be non-threaded and/or opening 26 can be non-threaded.

The support screw 30 has a distal end portion and a proximal end portion with a shaft 34 extending therebetween. The distal end portion 37 is extended through the opening 16 of plate 12 and through the opening 26 (either slid through or threaded through). The support screw 30 in the embodiment of FIG. 1A is made of machined implant grade stainless steel, but could alternatively be made of machined Titanium 6Al-4V ELI, implant grade additive manufacturing materials such as Titanium Grade 2 or OsteoFab PEKK. In the embodiment of FIG. 1A, shaft 34 of beaming screw 30 has an outside diameter having a value in the range of about 2 mm to about 3.5 mm mm and support screw 20 has a length having a value in the range of about 16 mm to about 38 mm.

Figure 1F:
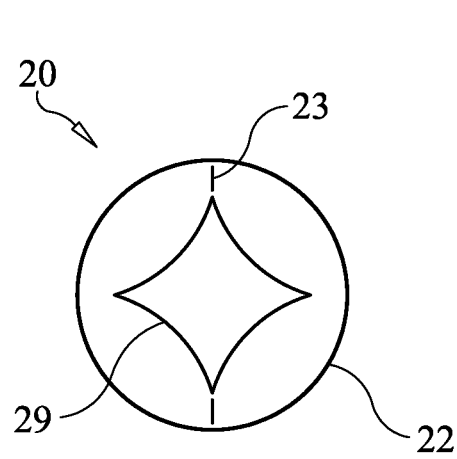
FIG. 1F shows a proximal end view of a beaming screw according to an embodiment of the present invention.

FIG. 1F shows a proximal end view of beaming screw 20 that includes a mark 23 on the screw head 22. In the embodiment of FIG. 1F, mark 23 is in addition to the driving receptacle 29 configured to mate with and be driven by a driver that drives the screw 20 into its implanted location. Alternatively, mark 23 may be incorporated as part of the driving receptacle. In either case, mark 23 indicates the orientation of opening 26. In the example shown, mark 23 aligns with the longitudinal axis of the opening 26. Thus, when mark 23 is aligned with the longitudinal axis of the locking plate 12 upon installation of beaming screw 20 therethrough, this indicates to the user that the opening 26 is properly aligned to receive the support screw 30 therethrough.

Figure 1G:
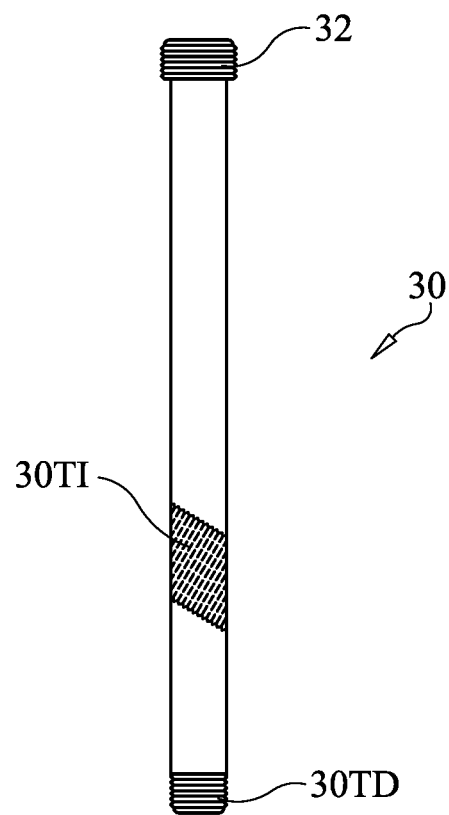
FIG. 1G shows a support screw according to an embodiment of the present invention.

FIG. 1G shows an embodiment of support screw 20 in which the distal end portion of screw 30 is threaded 30TD and the head 32 of the screw 30 at the proximal end portion is threaded 30TP. An intermediate portion of the screw 30 on screw shaft 34 is also threaded 30TI with threads configured and dimensioned to mate with the threads 26T in opening 26 of beaming screw 20. Screw 30 is cannulated in the embodiment of FIG. 1F, allowing it to be guided over a K wire. In alternative embodiments, head 32 can be non-threaded. Further alternatively, threading 30TI may be the same as threading 30TD or may continuously extend from threading 30TD. Further alternatively, screw 30 may be provided without threading 30TI in embodiments where screw shaft 34 is configured to slide through opening 26.

Figure 2:
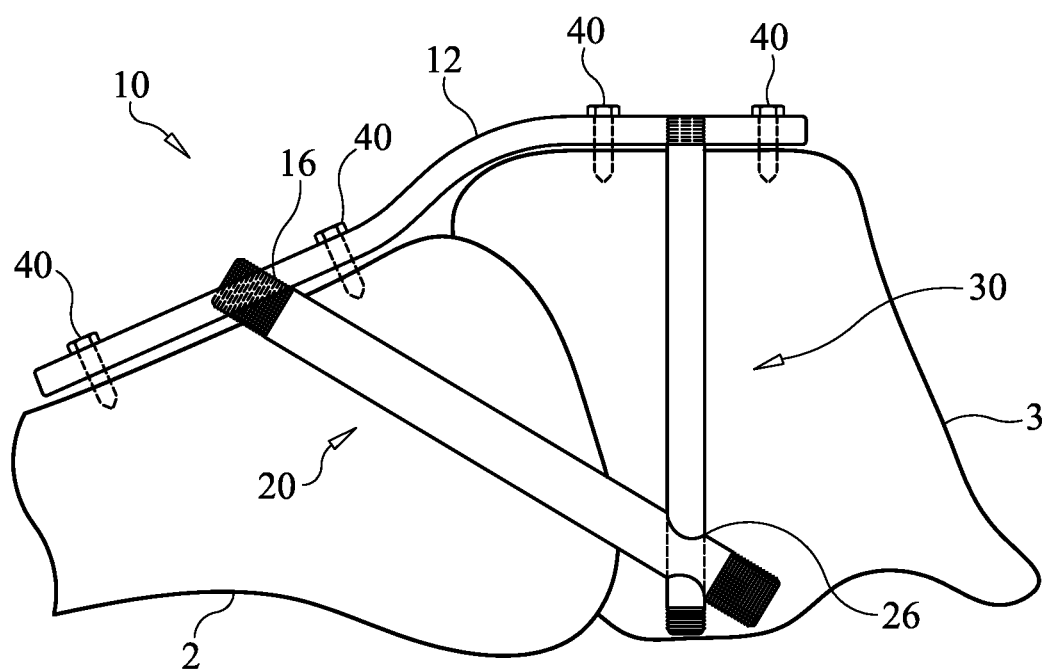
FIG. 2 illustrates a securement apparatus as secured in the foot and fixing together the adjacent bones in the foot of a human patient, according to an embodiment of the present invention.
Figure 3:
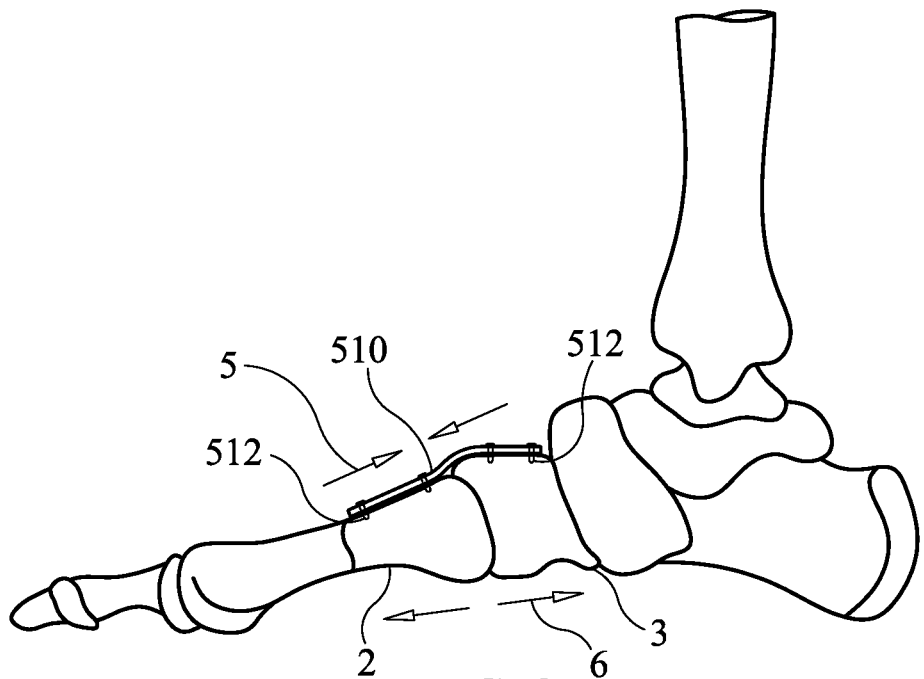
FIG. 3 illustrates a prior art plate fixation lapidus medical device fixed in a human foot.
Figure 4:
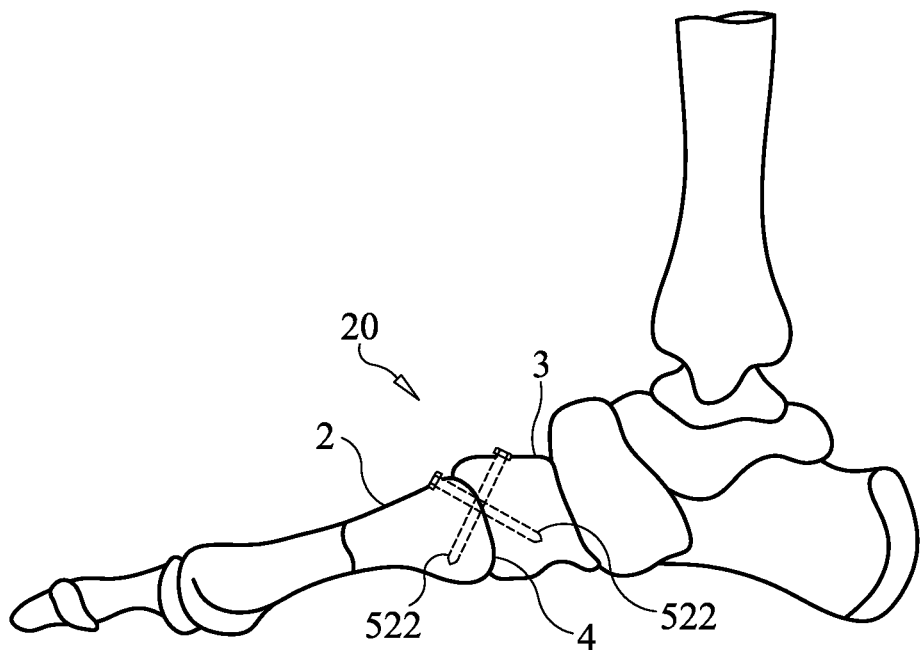
FIG. 4 illustrates a prior art crossing screw fixation method for lapidus showing crossing screws fixed in a human foot.

FIG. 2 illustrates the apparatus 10 of FIG. 1A having been implanted in the foot of a patient, according to an embodiment of the present invention. The first metatarsal bone 2 and medial cuneiform bone 3 are adjacent bones in a foot. In multiple foot surgeries, these two bones 2 and 3 must be fused or secured rigidly together. As shown in FIG. 2 a locking plate 12 is fixed to the top or dorsal side of the first metatarsal bone 2 and medial cuneiform bone 3. Shown in dashed lines are the optional locking screws 40 used to fix the locking plate 12 to the bones 2 and 3. The distal end portion of beaming screw 20 has been passed through opening 14 of locking plate 12, through a portion of bone 2 and screwed into the medial cuneiform bone 3 thereby rigidly fixing the beaming screw 20 therein.

The threaded head 22 of beaming screw 20 is screwed to the mating threads in opening 14, thereby locking the beaming screw 20 in rigid attachment to the locking plate 12. The beaming screw 20 further includes a threaded opening 26 therein that is adapted to receive the support screw 30. The support screw 30 extends through a portion of the bone 3 and is passed through the opening 26 and screwed into the bone 3 thereby rigidly fixing the support screw 30 in the bone 3. The screw 30 may also threadably engage the opening 26 for further securement and rigidization of the apparatus. Alternatively, the screw 30 may slide through the opening, with the rigidity provided by the threading of screws 20 and 30 into the bone 3 and into locking plate 12.

In all of these alternatives, the support screw 30 and beaming screw 20 are rigidly fixed to each other and to locking plate 12. The resulting structure is a triangular structure made up of the three sides of a locking plate 12, beaming screw 20, and support screw 30. This support structure creates a much more rigid and thorough support then the prior art plate fixation lapidus and crossing screw fixation combination for lapidus systems or other bone plate apparatus known in the art.

FIGS. 5A-5L illustrate procedural steps that may be carried out in implanting an apparatus 10 according to an embodiment of the present invention. In this procedure the apparatus 10 provides a hybrid of a locking plate 12 with a beaming screw 20 through it, which compresses the arthrodesis site and is locked by a second locking screw (i.e., support screw 30). The support screw 30 goes through the locking plate 12 and engages the distal portion of the large beaming screw 20 directly through its mid substance, locking the screws 20, 30 and the plate 12 in a rigid alignment which cannot be displaced by the forces applied during use of the foot.

FIGS. 5A-5L illustrate examples of steps that can be performed for the fusion of the first metatarsal bone 2 to the medial cuneiform bone 3 according to an embodiment of the present invention. Surgery is undertaken with a dorsal incision of the foot, and the joint surfaces of the first metatarsal bone 2 and medial cuneiform bone 3 are identified. The articular cartilage at the identified joint surfaces is resected by the manner of choice of the surgeon. With the joint surfaces prepared according to surgeon's preference a guide pin 50 (e.g., a 2 K wire) is placed across the osteotomy from dorsal distal to proximal plantar, passing through a portion of first metatarsal bone 2 and medial cuneiform bone 3, as illustrated in the top and side views of FIGS. 5A-5B, respectively.

The locking plate 12 is loosely placed over the guide pin and slid into position by sliding the opening 14 over the guide pin 50 (see top and side views in FIGS. 5C-5D, respectively), so that the screw 20 that follows the guide pin 20 will lock to the plate 12. Optionally, but preferably, one or more locking screws 40 should be installed at this time to secure the relative position of the locking plate 12 to the bone(s).

Figure 5A:
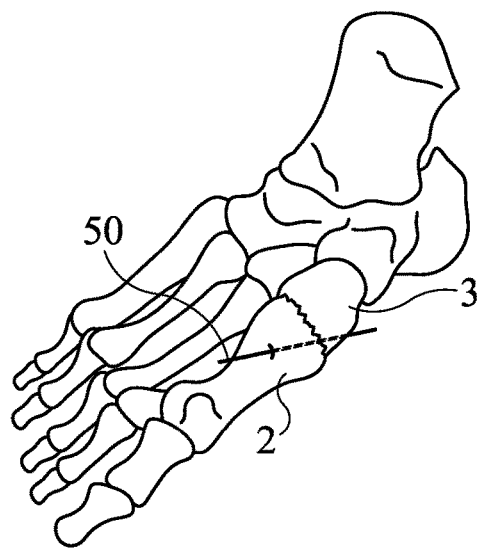
FIGS. 5A-5N illustrate procedural steps that may be carried out in implanting an apparatus according to an embodiment of the present invention.
Figure 5B:
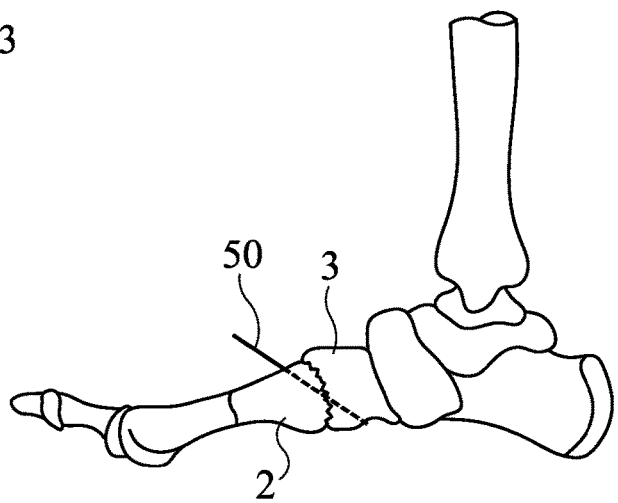
Figure 5C:
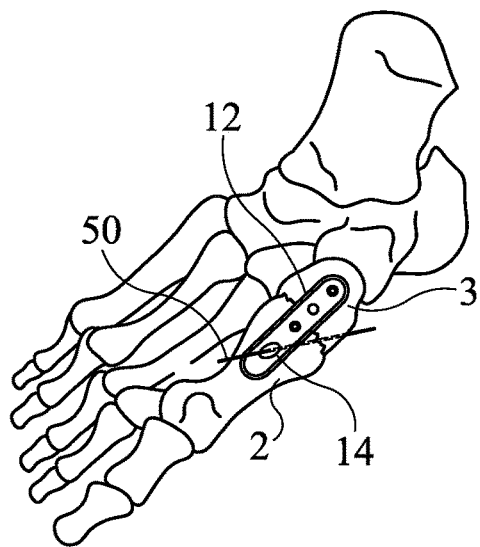
Figure 5D:
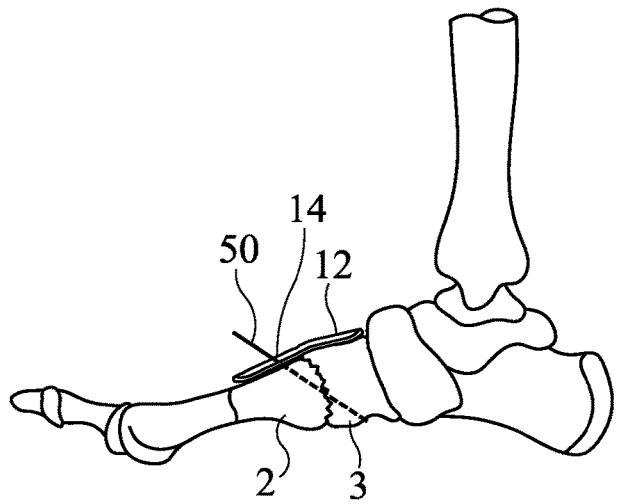
Figure 5E:
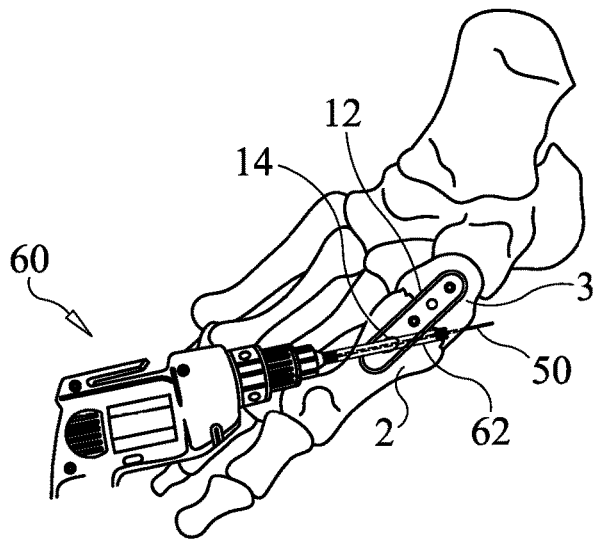
Figure 5F:
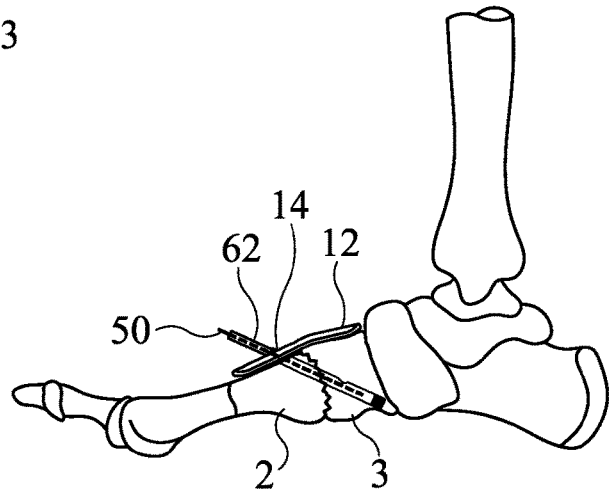

A drill 60 having a cannulated drill bit 62 is next used to drill over the guide pin 50 and a depth gauge is used so that the drill hole formed by the drilling is gauged to the length of the beaming screw 20 to be implanted therein, see FIGS. 5E and 5F (FIG. 5F showing the drill bit 62 without the drill 60 to better illustrate the guide pin 50). The drill hole may be slightly less in length that the beaming screw 20 when the beaming screw is provided with a self-drilling and self-tapping distal threaded tip. Alternatively, the length of the drill hole may be equal to or slightly greater than the length of the beaming screw 20.

Figure 5G:
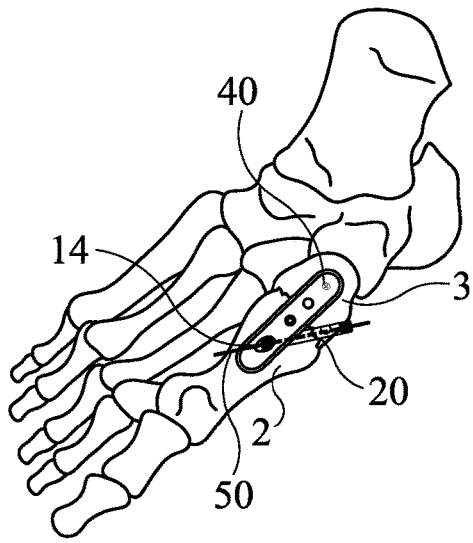

After drilling the drill hole to the appropriate, predetermined length and removing the drill 60 and drill bit 62, a beaming screw 20 of predetermined length, to which the length of the drill hole has been gauged, is installed through the opening 14 and into the drill hole, where it is screwed into the medial cuneiform bone 3 using a driving tool. The head 22 of the beaming screw 20 is at the same time screwed into the threads of the opening 14, thereby locking the beaming screw 20 to the locking plate 12 and the medial cuneiform bone 3 as illustrated in FIG. 5G. Upon locking the head 22 to the beaming plate 12, the head is rotated until the mark 23 (see FIG. 1F) indicates that the opening 26 is properly oriented to receive support screw 30. The guide pin 50 is then removed by withdrawing it out of the cannula 27 (cannula 27 is illustrated in FIG. 1A). A locking screw 40 (see FIGS. 5G-5H) on the cuneiform side of the osteotomy firmly locks the plate 12 down to the medial cuneiform bone 3 on other side of the osteotomy.

Figure 5H:
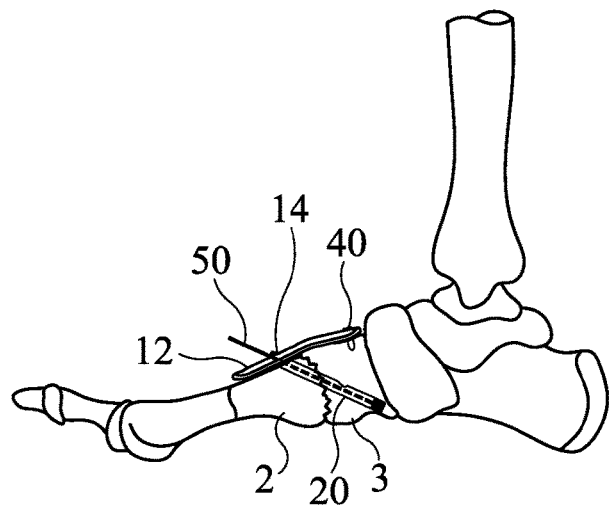
Figure 5I:
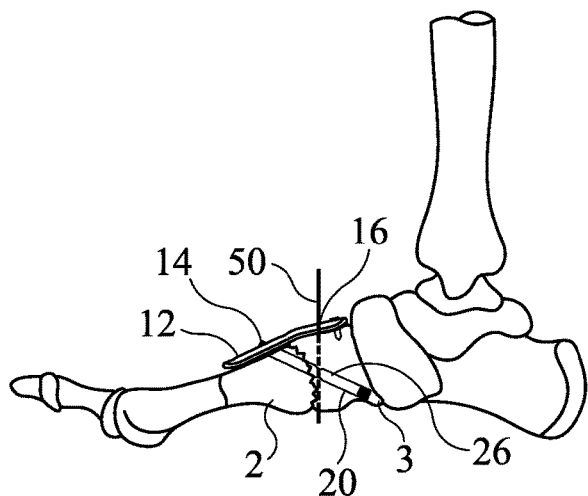
Figure 5J:
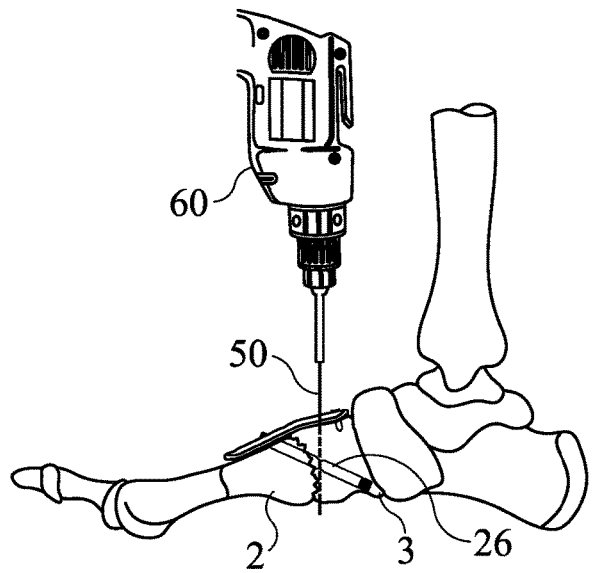

At FIGS. 5I-5H another guide pin (e.g., K wire) 50 is introduced into the proximal side of the plate 12 through opening 16 and passed through the opening 26 in beaming screw 20, see FIGS. 5I-5J. Fluoroscopic imaging may be employed to confirm that the guide pin 50 has passed through the opening 26.

Figure 5K:
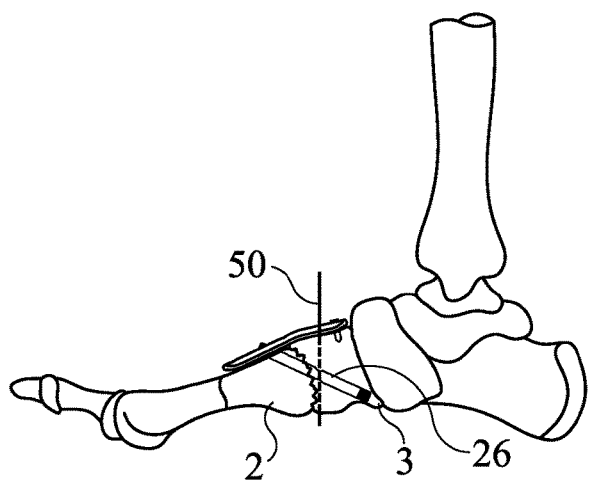
Figure 5L:
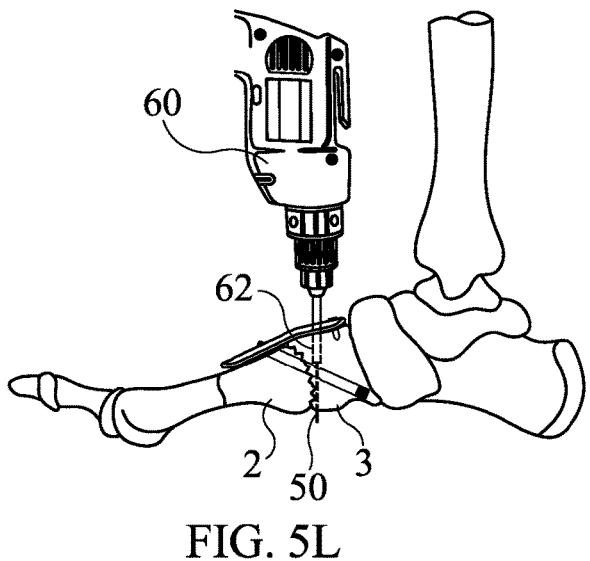

Next, as illustrated in FIGS. 5K-5L, a drill 60 having a cannulated drill bit 62 is placed over the guide pin 50 and used to drill a drill hole down from the locking plate 12 through the opening 26 and to a predetermined length which may be gauged to a length of a support screw 30 to be used. Like the drill hole for beaming screw 20, a depth gauge may be used to determine the depth (length) of the hole drilled for the support screw 30.

Figure 5M:
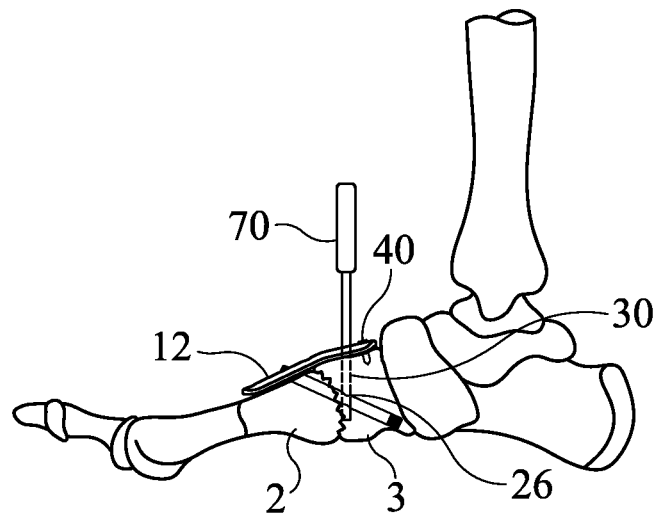
Figure 5N:
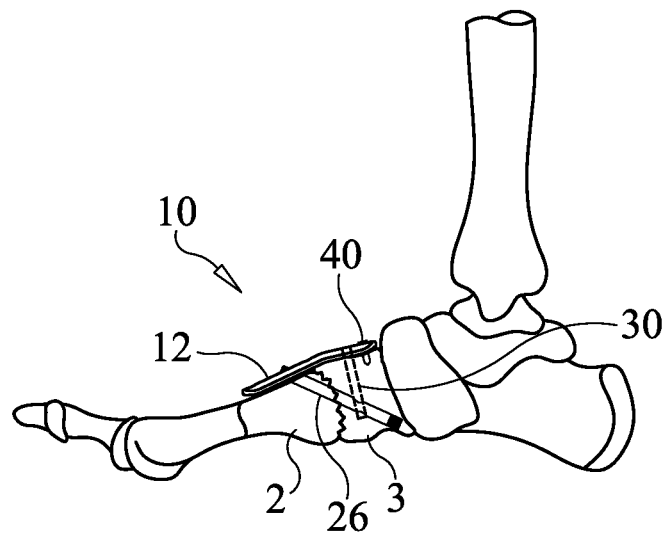

After drilling the drill hole to the appropriate, predetermined length (depth) and removing the drill 60 and drill bit 62, a support screw 30 of predetermined length, to which the length of the drill hole has been gauged, is installed through the opening 16 and into the drill hole, where it is screwed into opening 26 and then into the medial cuneiform bone 3 using a driving tool 70, see FIG. 5M, thereby locking the support screw 30 to the beaming screw 20, the locking plate 12 and the medial cuneiform bone 3. The guide pin 50 is then removed by withdrawing it out of the cannula of the support screw 30. The implantation of apparatus 10 has been completed at this stage. As shown in FIG. 5N, the apparatus 10 includes the locking plate 12, beaming screw 20 and support screw 30 all rigidly connected to form a rigid, triangular structure (buttress). Having completed the implantation, the remaining surgical steps for closure of the tissues, suturing, bandaging, etc. can be carried out according to known best practices.

Figure 6A:
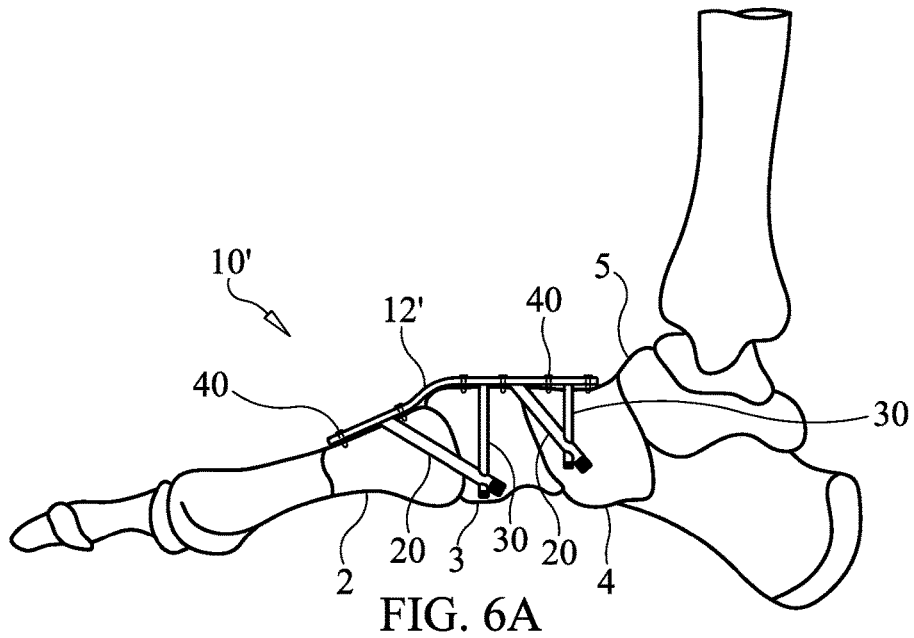
FIG. 6A illustrates an apparatus implanted in the foot of a patient to form two buttresses/triangular structures, according to an embodiment of the present invention.
Figure 6B:
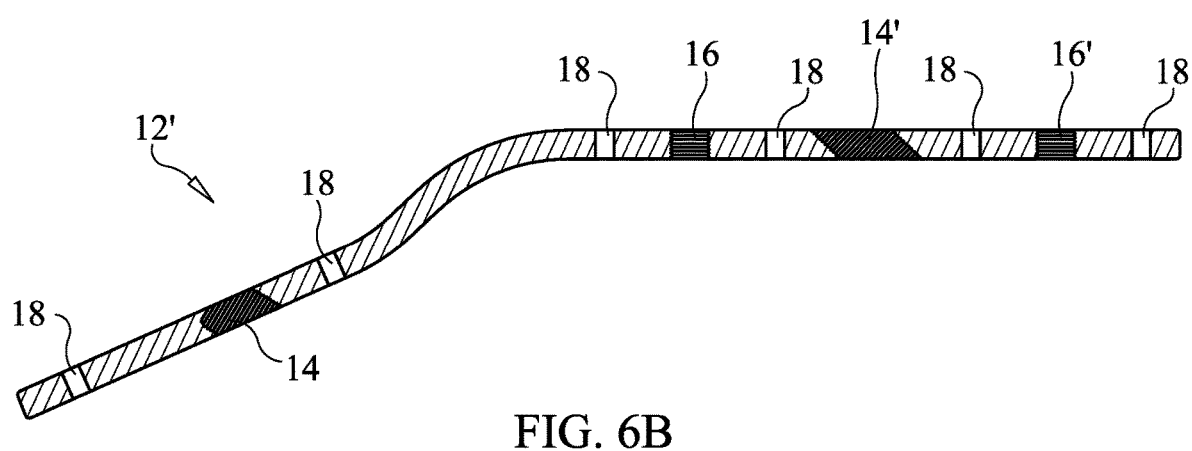
FIG. 6B is a longitudinal sectional view of the locking plate of the embodiment of FIG. 6A.

It is noted that the present invention is not limited to the formation of a single buttress/triangular structure, as two or more such buttresses can be formed by an apparatus where desirable. FIG. 6A illustrates an apparatus 10' implanted in the foot of a patient to form two buttresses/triangular structures. In this embodiment, locking plate 12' is configured and shaped to overlie and conform to at least portions of the first metatarsal 2, medial cuneiform 3, navicular 4 and talus 5 bones. As shown in FIG. 6B, locking plate 12' includes openings 14' and 16' in addition to openings 14 and 16. In addition to formation of the first buttress (left most buttress in FIG. 6A) in the same manner as described with regard to FIGS. 5A-5N above, a second buttress is formed in a similar manner.

A guide pin 50 is inserted through opening 14', through the medial cuneiform 3, navicular 4 and into the talus 5 bone. A drill 60 having a cannulated drill bit 62 is next used to drill over the guide pin 50 and a depth gauge is used so that the drill hole formed by the drilling is gauged to the length of the beaming screw 20 to be implanted therein. The drill hole may be slightly less in length that the beaming screw 20 when the beaming screw is provided with a self-drilling and self-tapping distal threaded tip. Alternatively, the length of the drill hole may be equal to or slightly greater than the length of the beaming screw 20.

After drilling the drill hole to the appropriate, predetermined length and removing the drill 60 and drill bit 62, a beaming screw 20 of predetermined length, to which the length of the drill hole has been gauged, is installed through the opening 14' and into the drill hole, where it is screwed into the talus bone 3 using a driving tool. The head 22 of the beaming screw 20 is at the same time screwed into the threads of the opening 14', thereby locking the beaming screw 20 to the locking plate 12' and the talus bone 3, while compressing the medial cuneiform 3, navicular 4 and talus 5 bones together. Upon locking the head 22 to the beaming plate 12', the head is rotated until the mark 23 indicates that the opening 26 is properly oriented to receiving support screw 30. The guide pin 50 is then removed by withdrawing it out of the cannula 27.

Another guide pin (e.g., K wire) 50 is introduced through opening 16' and passed through the opening 26 in beaming screw 20. Fluoroscopic imaging may be employed to confirm that the guide pin 50 has passed through the opening 26. Next, a drill 60 having a cannulated drill bit 62 is placed over the guide pin 50 and used to drill a drill hole down from the locking plate 12' through the opening 26 and to a predetermined length which may be gauged to a length of a support screw 30 to be used. In this example, the drill hole terminates in the talus bone. Like the drill hole for beaming screw 20, a depth gauge may be used to determine the depth (length) of the hole drilled for the support screw 30.

After drilling the drill hole to the appropriate, predetermined length (depth) and removing the drill 60 and drill bit 62, a support screw 30 of predetermined length, to which the length of the drill hole has been gauged, is installed through the opening 16' and into the drill hole, where it is screwed into opening 26 and then into the talus bone 5 using a driving tool 70, thereby locking the support screw 30 to the beaming screw 20, the locking plate 12' and the talus bone 5. The guide pin 50 is then removed by withdrawing it out of the cannula of the support screw 30. The implantation of apparatus 10' has been completed at this stage. As shown in FIG. 6A, the apparatus 10 includes the locking plate 12', two beaming screws 20 and two support screws 30 all rigidly connected to form two rigid, triangular structures (buttresses).

Figure 7A:
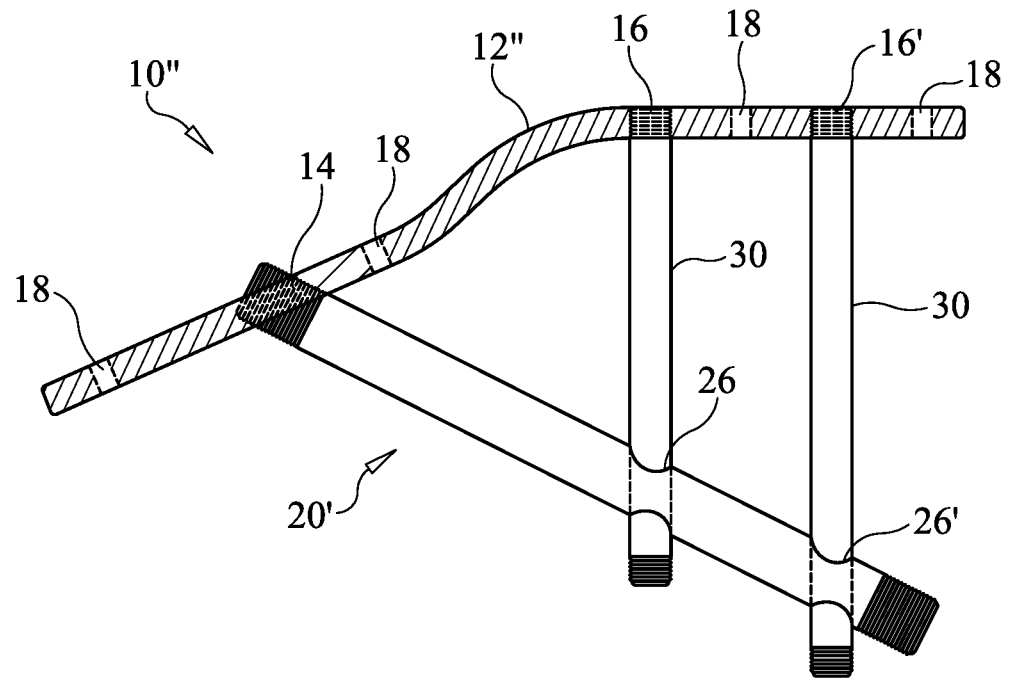
FIG. 7A illustrates a securement apparatus according to an embodiment of the present invention.
Figure 7B:
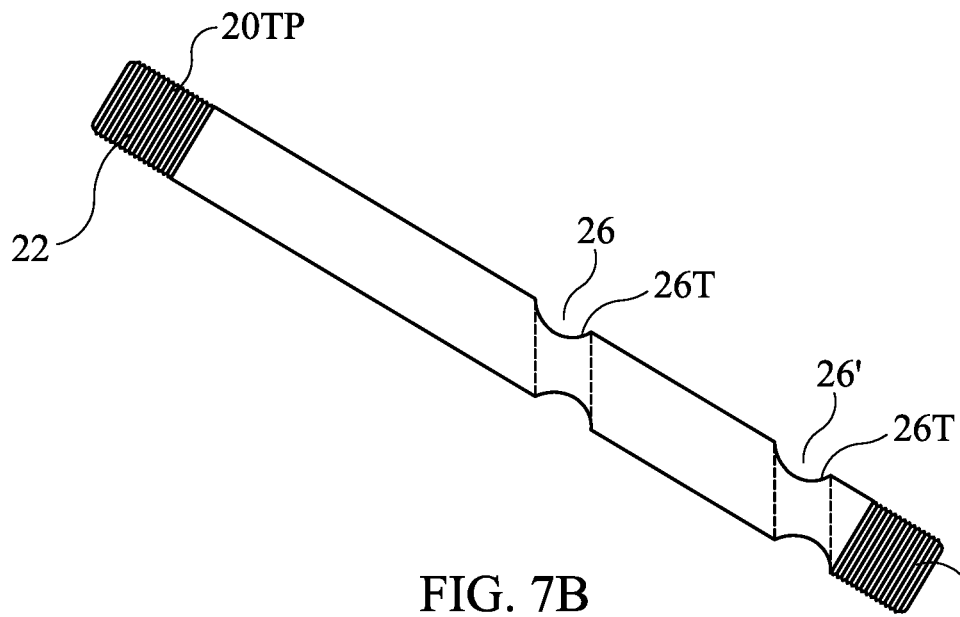
FIG. 7B is an isolated view of the beaming screw shown in FIG. 7A.
Figure 8A:
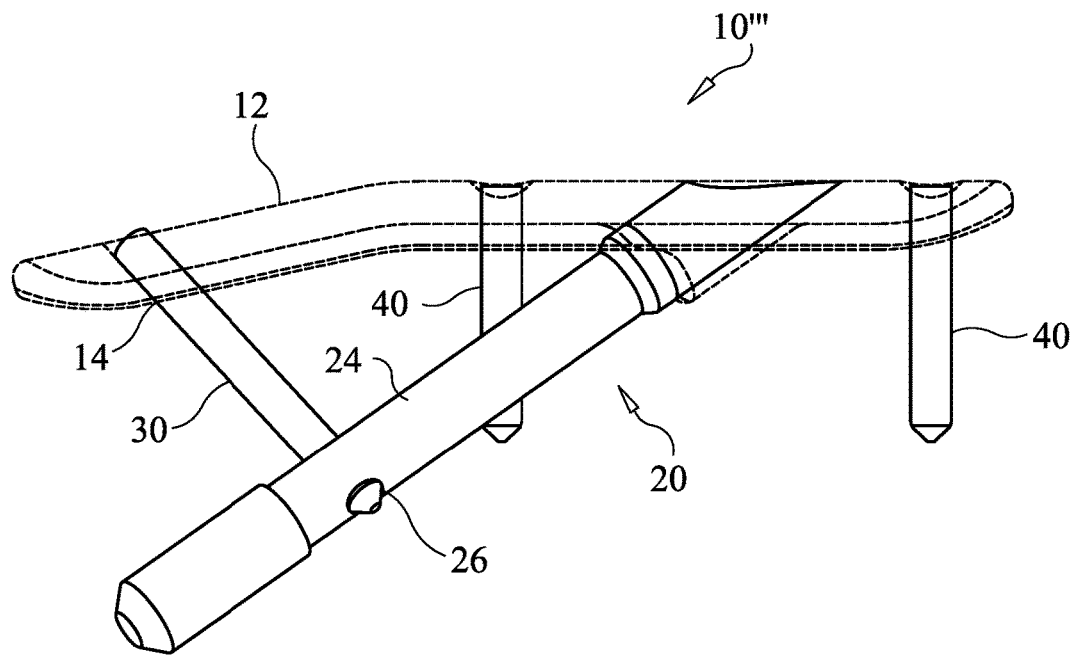
FIGS. 8A-8D are schematic illustrations of a side view, perspective view, bottom view and end view of a securement apparatus according to an embodiment of the present invention.
Figure 8B:
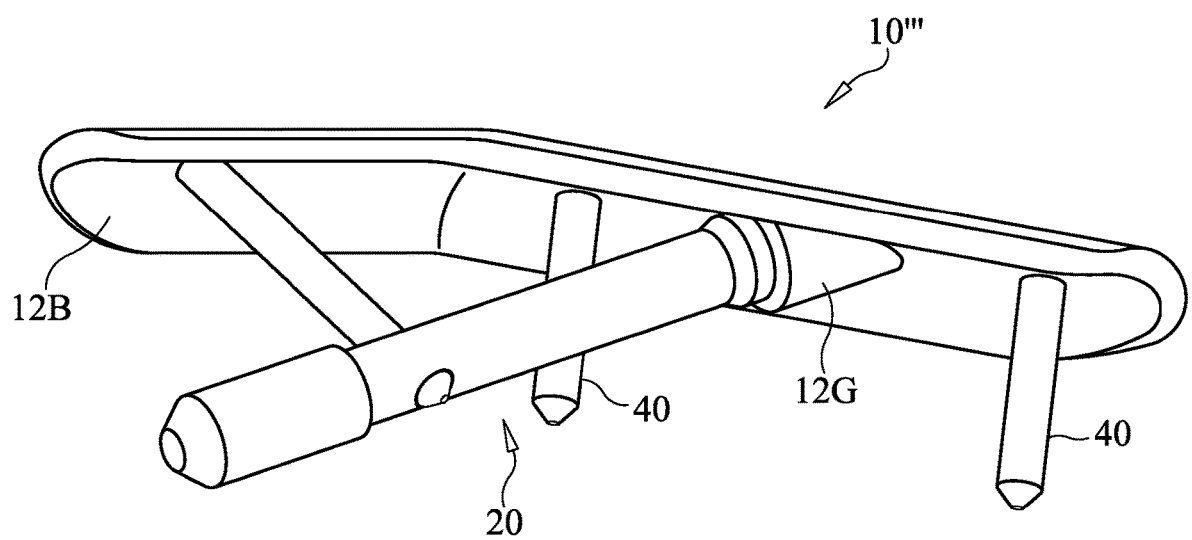
Figure 8C:
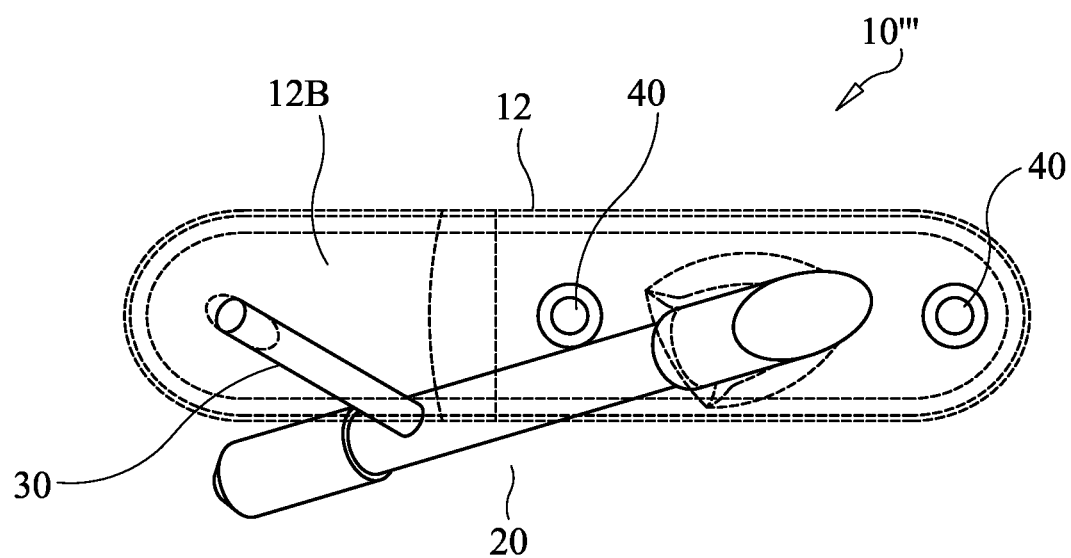
Figure 8D:
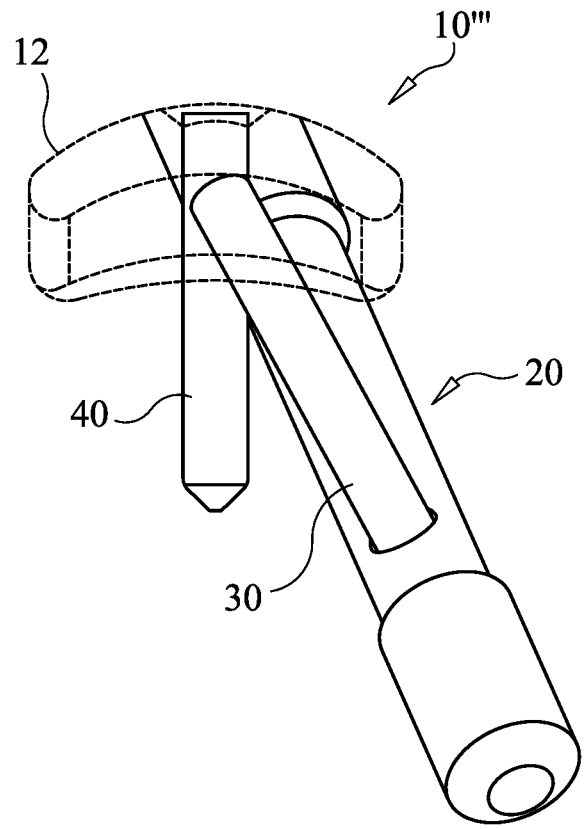

FIG. 7A illustrates an apparatus 10" according to another embodiment of the present invention. In this embodiment, locking plate 12" is provided with opening 14 to receive beaming screw 20' and openings 16 and 16' to receive two support screws 30. The beaming screw 20' is provided with two openings 26, 26' spaced, sized and dimensioned to receive respective support screws 30, see FIG. 7B. Openings 26, 26' can be aligned with openings 16, 16' through use of mark 23 in a manner as described above. After installation of beaming screw 20' through locking plate 12" in a manner as described with regard to beaming screw 20 above, support screws 30 are installed though openings 26, 26' in a manner as described above with regard to installing support screw 30 through locking plate 12 and opening 26.

The apparatus of the invention can thus be modular, as it can be used across one joint that is to be arthrodesed as well as be utilized across multiple joints to be arthrodesed. An example of the second instance is for Charcot reconstruction, where the medial column including Lisfranc joint and the midtarsal joint both require arthrodesis in an anatomic position, such as illustrated above with regard to FIG. 6A.

In multi-joint arthrodesis, multiple triangulated locked segments independent of each other can be established, as in FIG. 6A. For ease of placement, a single large diameter guidepin can be placed down the medial column from the metatarsal head to the body of the talus. This could anatomically reconstruct the segment in appropriate position of function. When the plate is placed with the triangulated constructs, it could be removed. According to an embodiment of the present invention, reconstruction for arthrodesis utilizes the benefits of a locking plate in combination with compression screw fixation and the addition of a second screw through the large diameter compression screw both attached to the plate to produce a triangle of strength.

As noted, the beaming screw 20 can have the single opening 26 therein to receive the support screw 30. Alternatively, as also noted, there can be multiple openings 26, 26' along the length of the beaming screw 20' in order to receive additional support screws 30 or to allow for alternative placement of the support screws. In at least one embodiment, the support screw 30 is a 2.5 mm diameter cannulated screw. This metal screw is likewise made of various steels or other metals or alloys thereof to create a rigid support screw 30.

The openings 14, 16 (and optionally, 14' and/or 16') of locking plate 12, 12', 12" may be angled to point the screws received therethrough towards each other so that the support screw 30 will align with the hole 26 in the beaming screw 20.

The, the locking plates 12, 12', 12" may include additional openings not shown along their lengths including openings having various geometries and directional inclines to direct various beaming screw or screws to respective support screw or screws.

In the embodiments shown, the bones joined are adjacent bones in a foot. The present invention can be used to secure any adjacent bones in the body that have a substantial enough size to receive the beaming screw 20 and support screw 30. Additionally, the present invention can be used for a single bone that may be fractured or otherwise requires support.

The triangular structure made up of the three sides of a locking plate 12, beaming screw 20, and support screw 30 creates a much more rigid and thorough support then the prior art plate fixation lapidus and crossing screw fixation combination for lapidus systems.

The locking plates 12, 12', 12" are shown as generally conforming to the outside contour of the bones of the foot to which they are mounted. Alternatively, the locking plates 12, 12', 12" can take other geometrics. Preferably, the locking plate 12, 12', 12" will have a profile or contour that matches or conforms to the bones to which it will be attached.

FIGS. 8A-8D are schematic illustrations of a side view, perspective view, bottom view and end view of an apparatus 10''' according to an embodiment of the present invention. This embodiment is similar to the embodiments of FIGS. 1A-2, so only the differences are described in detail here. In this embodiment, support screw 30 forms an acute angle with locking plate 12 in a direction toward beaming screw 20, as differentiated from the substantially normal angle formed by the embodiment of FIGS. 1A-2. However, it is noted that the embodiments of FIGS. 1A-2 could be modified so as to employ such an acute angle. Likewise the embodiment of FIGS. 8A-8D could be modified so that support screw 30 is substantially normal to the locking plate 12 where it joins the locking plate 12.

The locking plate 12 of FIGS. 8A-8D is nonplanar such that the surface 12B configured to contact the bone is concave or other nonplanar shape that more closely fits to the bones that it contacts. However, contact to the bones along all of the surface 12B (or bone contacting surface of any of the other embodiments described herein) is not required for optimal functioning of the device 10, 10', 10", 10''' due to the configuration formed by the components 12, 20 and 30. Close fitting of the locking plate is desirable for better conformance to the bones with less interference of the implant with external objects, such as shoes and socks, as well as to provide a better visual appearance. Additionally, a guide 12G extends from the bottom surface 12B of the locking plate, which functions as a jig so that the locking plate 12 can act as its own jig for use in alignment with the beaming screw 20 during installation.

Figure 9A:
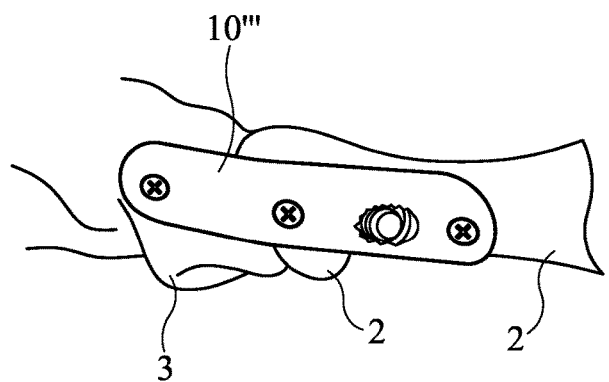
FIGS. 9A-9B illustrate the apparatus of FIGS. 8A-8D implanted on the metatarsal and cuneiform bones of a foot, according to an embodiment of the present invention.
Figure 9B:
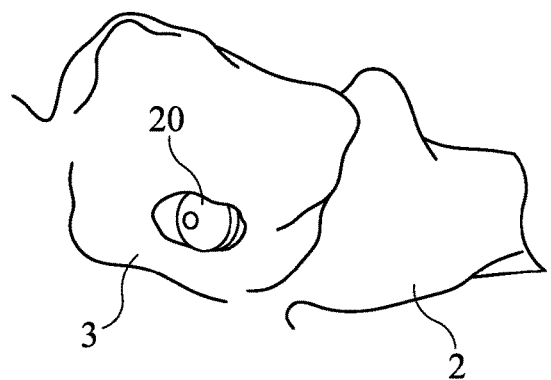
Figure 10:
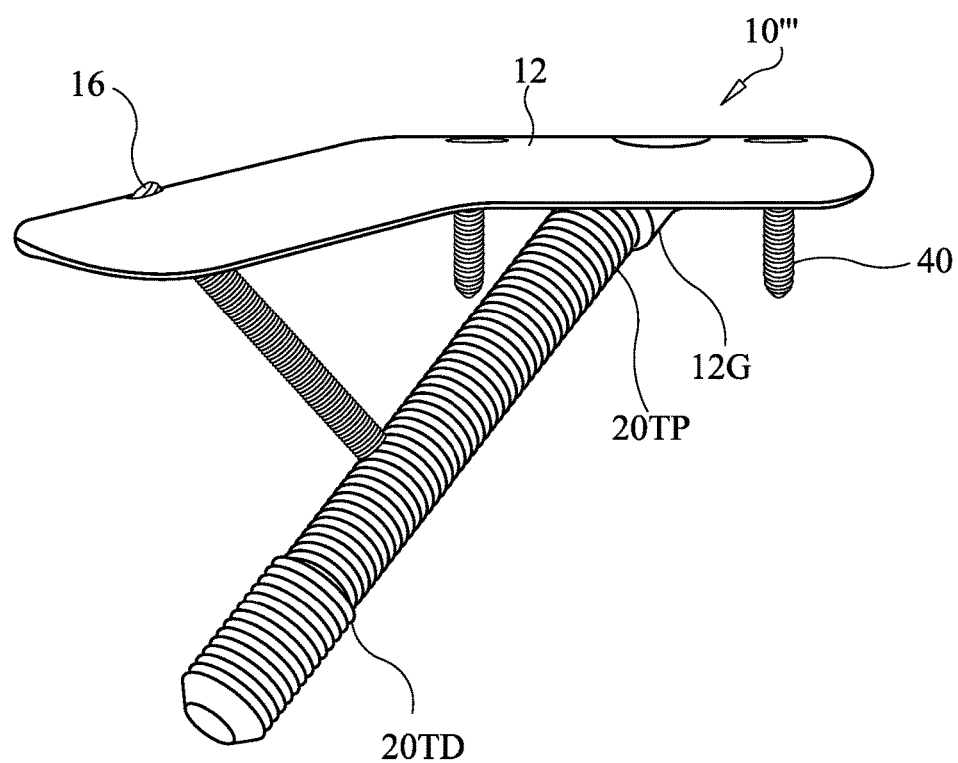
FIG. 10 is an illustration of a securement apparatus according to an embodiment of the present invention.

FIGS. 9A-9B illustrate the apparatus 10''' implanted on the metatarsal 2 and cuneiform 3 bones of a foot. FIG. 10 is another illustration of an apparatus 10''' that shows the threading 16, 20TD, 20TP and threading on the screws.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

The invention claimed is:

1. A method of implanting a bone securement apparatus, said method comprising: placing a bone plate across a joint of at least two bones or a space between at least two bone fragments, said bone plate comprising first and second openings; inserting a beaming member through said first opening, a portion of a first of said bones or bone fragments and a portion of a second of said bones or bone fragments; wherein said beaming member comprises a third opening that is positioned in the second of said bones or bone fragments upon said inserting; and inserting a support member through said second opening and said third opening, wherein said beaming member has a first length and said support member has a second length, said first length being greater than said second length.

2. The method of claim 1, further comprising attaching said beaming member to the second of said bones or bone fragments via threading on said beaming member.

3. The method of claim 1, further comprising attaching said support member to the second of said bones or bone fragments via threading on said support member.

4. The method of claim 1, further comprising threading said support member into mating threads in said third opening.

5. The method of claim 1, further comprising attaching said bone plate to at least one of said first and second bones or bone fragments by inserting a locking screw through at least one additional opening in said bone plate and threading said locking screw into said at least one of said first and second bones or bone fragments.

6. The method of claim 1, wherein said bone plate, beaming member and support member form a triangular structure.

7. The method of claim 1, wherein said bone plate further comprises fourth and fifth openings, said method further comprising:

inserting a second beaming member through said fourth opening, and into at least one of said bones or bone fragments or at least a third bone or bone fragment and at least a third bone fragment, wherein said second beaming member comprises a sixth opening; and inserting a second support member through said fifth opening and said sixth opening.

8. The method of claim 1, wherein said first bone or bone fragment comprises a first metatarsal bone and said second bone or bone fragment comprises a medial cuneiform bone.

9. The method of claim 7, wherein said first bone or bone fragment comprises a first metatarsal bone, said second bone or bone fragment comprises a medial cuneiform bone, said at least one of said bones or bone fragments comprises said medial cuneiform bone and said at least a third bone or bone fragment comprises at least one of a navicular bone and a talus bone.

10. The method of claim 1, wherein at least one of the bones or bone fragments is in a foot or ankle.

11. The method of claim 1, wherein said method is performed for reconstruction of a Charcot foot.

12. A method of implanting a bone securement apparatus, said method comprising: placing a bone plate across a joint of at least two bones or a space between at least two bone fragments, said bone plate comprising first and second openings; inserting a beaming member through said first opening, a portion of a first of said bones or bone fragments and a portion of a second of said bones or bone fragments; wherein said beaming member comprises a third opening that is positioned in the second of said bones or bone fragments upon said inserting; and inserting a support member through said second opening, a portion of the second of the bones or bone fragments and said third opening, wherein said beaming member has a first length and said support member has a second length, said first length being greater than said second length.

13. The method of claim 12, wherein at least one of the bones or bone fragments is in a foot or ankle.

14. The method of claim 12, wherein said method is performed for reconstruction of a Charcot foot.

* * * * *